(12) United States Patent
Tsuchiya et al.

(10) Patent No.: US 8,903,158 B2
(45) Date of Patent: Dec. 2, 2014

(54) INSPECTION SYSTEM AND INSPECTION METHOD

(75) Inventors: Hideo Tsuchiya, Tokyo (JP); Takafumi Inoue, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 511 days.

(21) Appl. No.: 12/856,901

(22) Filed: Aug. 16, 2010

(65) Prior Publication Data

US 2011/0044529 A1  Feb. 24, 2011

(30) Foreign Application Priority Data

Aug. 18, 2009  (JP) ................ 2009-189606

(51) Int. Cl.
  *G06K 9/00* (2006.01)
  *G03F 1/84* (2012.01)
  *G01N 21/88* (2006.01)
  *G01N 21/956* (2006.01)

(52) U.S. Cl.
  CPC ...... *G01N 21/95607* (2013.01); *G01N 21/8851* (2013.01); *G06T 2207/30148* (2013.01); *G01N 2021/95676* (2013.01); *G03F 1/84* (2013.01)
  USPC ........... 382/149; 382/144; 382/145; 382/147; 382/148

(58) Field of Classification Search
  CPC ............................... G06T 2207/30148
  USPC ......................... 382/144, 147, 149
  See application file for complete search history.

(56) References Cited

U.S. PATENT DOCUMENTS

| 5,602,890 A * | 2/1997 | Gray et al. ...................... 378/57 |
| 2004/0008880 A1 | 1/2004 | Horie et al. |
| 2007/0237385 A1* | 10/2007 | Kato ............................. 382/149 |

(Continued)

FOREIGN PATENT DOCUMENTS

| JP | 9-63944 | 3/1997 |
| JP | 2001-266126 | 9/2001 |
| JP | 2008-82740 | 4/2008 |
| JP | 2008-112178 | 5/2008 |

OTHER PUBLICATIONS

Japanese Office Action issued May 6, 2011, in Japanese Patent Application No. 2009-189606 with English translation.
U.S. Appl. No. 13/017,641, filed Jan. 31, 2011, Tsuchiya et al.

(Continued)

*Primary Examiner* — Ryan Zeender
*Assistant Examiner* — Hunter Wilder
(74) *Attorney, Agent, or Firm* — Oblon, Spivak, McClelland, Maier & Neustadt, L.L.P.

(57) ABSTRACT

An inspection system determines, for each detected pattern defect, a defect inspection pattern area of predetermined dimensions containing the coordinates of the defect, then determines the clusters or cells whose reference points are located within the defect inspection pattern area. The system extracts the data of these clusters or cells from design pattern data read from a first magnetic disk unit. The system then generates an output file containing the extracted data. The output file is then converted into the same format as the input design pattern data or into OASIS format, before it is output to a second magnetic disk unit. The extracted pattern data specifying the clusters or cells within each defect inspection pattern area can be output from the mask inspection system to external systems.

16 Claims, 7 Drawing Sheets

(56) References Cited

U.S. PATENT DOCUMENTS

| | | |
|---|---|---|
| 2009/0074286 A1 | 3/2009 | Kitazawa et al. |
| 2009/0136121 A1 | 5/2009 | Nakagaki et al. |
| 2009/0180680 A1* | 7/2009 | Satou et al. .................. 382/144 |
| 2009/0238441 A1* | 9/2009 | Yamashita .................... 382/144 |
| 2009/0238446 A1* | 9/2009 | Kataoka et al. ............... 382/152 |
| 2011/0044528 A1 | 2/2011 | Tsuchiya et al. |

OTHER PUBLICATIONS

C.Y. Chen, et al., "Mask Defect Auto Disposition based on Aerial Image in Mask Production", Proceedings of the SPIE. vol. 7379, 2009, pp. 73791F/1-11.

U.S. Appl. No. 13/768,392, filed Feb. 15, 2013, Inoue, et al.

U.S. Appl. No. 13/792,364, filed Mar. 11, 2013, Inoue, et al.

\* cited by examiner

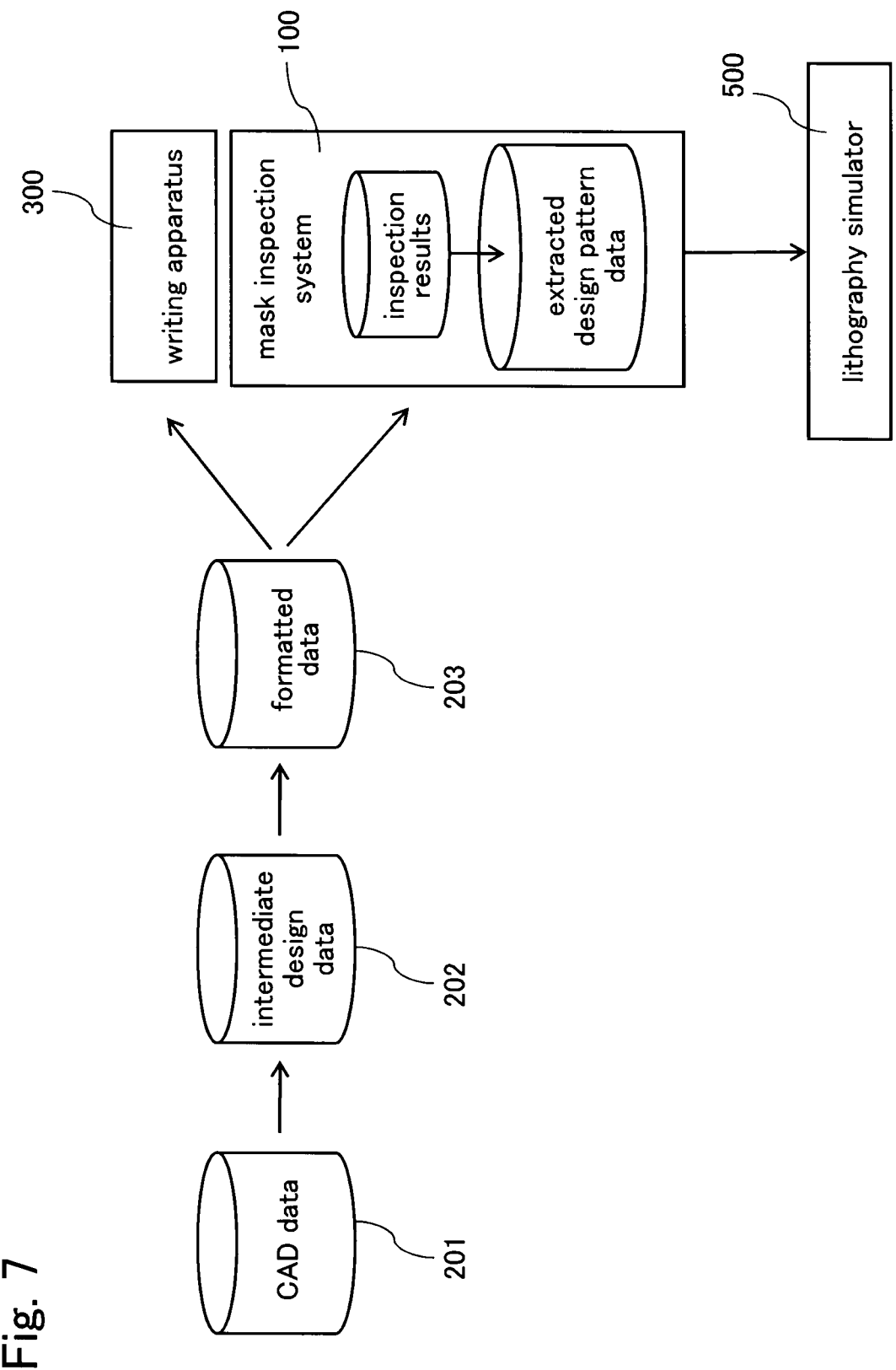

INSPECTION SYSTEM AND INSPECTION METHOD

BACKGROUND OF THE INVENTION

1. Field of the Invention

The present invention relates to an inspection system and an inspection method, and more particularly to an inspection system and an inspection method for detecting defects of the pattern formed on an object to be inspected, such as a mask.

2. Background Art

In recent years, as the levels of integration and capacity of large scale integrated circuits (LSIs) increase, there has been a need to continue to reduce the width of the circuit patterns of semiconductor devices. Semiconductor devices are manufactured by a reduced projection exposure apparatus called a "stepper" using original artwork patterns with a circuit pattern formed thereon, that is, masks or reticles (hereinafter referred to collectively as masks). Specifically, the pattern on a mask is transferred to the wafer by exposure to light, thereby forming circuits on the wafer. Masks used to transfer such fine circuit patterns to the wafer are manufactured by electron beam writing apparatuses, which can write micropatterns. Further, effort has been made to develop a laser beam writing apparatus, which uses a laser beam for writing. It should be noted that electron beam apparatuses are also used to directly write a circuit pattern on a wafer.

Incidentally, since the cost to manufacture LSIs is very high, the improvement of the yield is required to make the manufacture economically feasible. However, the dimensions of the patterns for LSI devices, as typified by 1-gigabit class DRAMs (random access memories), are about to be scaled down from the order of submicrons to the order of nanometers. A major cause of loss in yield is due to defects of a mask pattern. Further, since there has been a decrease in the dimensions of LSI patterns formed on semiconductor wafers, the size of pattern defects to be detected is very small. Therefore, high inspection accuracy is required of mask inspection systems for detecting defects of transfer masks used in LSI manufacture.

There are two known mask defect detecting methods: the die-to-die inspection method and the die-to-database inspection method. The die-to-die inspection method is used when the mask to be inspected has thereon a plurality of identical chip patterns, or a plurality of chip patterns each including an identical pattern segment. In this method, these identical chip patterns or identical pattern segments, which are located on the same mask, are compared to each other. This method permits accurate inspection using a relatively simple system configuration, since patterns on the same mask are directly compared to each other. However, this method cannot detect a defect common to both compared patterns. In the die-to-database inspection method, on the other hand, an actual pattern on a mask is compared to reference data generated from the design pattern data that was used to manufacture the mask. Thus, this method allows exact comparison of the pattern with the design pattern data, although the required system size is large since the method requires a processing system for generating a reference image. There is no choice but to use this inspection method when the mask to be inspected has only one chip pattern to be transferred to the wafer.

In die-to-die inspection system, light is emitted from a light source, and the mask to be inspected is irradiated with this light through an optical system. The mask is mounted on a table, and this table is moved so that the emitted beam of light scans the surface of the mask. Light transmitted through or reflected from the mask pass through the lens and are received by image sensors via a lens, thereby forming an image thereon. The optical image thus formed on the image sensor is sent to a comparing unit as the acquisition data. The comparing unit compares the acquisition data with reference data in accordance with an appropriate algorithm, and if they are not identical, the mask is determined to have a defect (see, e.g., Japanese Laid-Open Patent Publication No. 2008-112178).

If the inspection system determines that the mask has a defect, the system stores the optical image and the corresponding reference image on which the detection of the defect is based, together with the coordinates of the defect. Upon completion of the inspection of the mask, the operator visually checks the pattern in which each defect was detected using the observing optical system in the inspection system. Alternatively, the optical image and the reference image of each defect stored in the inspection system may be displayed on the display of the computer so that the operator can easily check the pattern. The operator then determines whether each defect requires a repair and sends to the repair system the mask and information necessary to repair the defects in need of repair. For example the necessary repair information regarding each defect includes: its coordinates in the mask; an indication of whether it is a extrusion defect (i.e., opaque defect), which must be removed from the light shielding film, or a intrusion defect (i.e., clear defect), which must be filled in; and extracted pattern data for recognizing the pattern portion to be repaired by the repair system. The pattern data may be derived from the above optical image stored in the inspection system.

The repair system then repairs the mask in accordance with the information received from the inspection system, that is, for example, the repair system burns off each extrusion defect from the light shielding film by a beam of light such as a focused ion beam (FIB) and fills each intrusion defect by deposition of carbon (see, e.g., Japanese Laid-Open Patent Publication No. 9-63944 (1997)). The repaired mask is then reinspected. Only repaired masks which have successfully passed the reinspection are shipped.

As pattern dimensions have been scaled down, new types of mask defects have been encountered. That is, current problems to be addressed include not only pattern edge irregularities, formation of isolated holes, and adhesion of material, but also subtle pattern line width errors and pattern displacement. A deviation in the pattern line width or in the spacing between adjacent patterns results in a change in the pattern's impedance and hence a change in the performance of the completed LSI. Such subtle defects may be detected by the mask inspection system using an improved defect detection algorithm. However, the repair information conventionally used to repair detected defects is not sufficient to allow the repair system to locate subtle pattern defects without difficulty even if they are detected by the inspection system. Therefore, there is an urgent need to improve the content of repair information.

The present invention has been made in view of the above problems. That is, since conventional repair information includes only optical images captured by the inspection system and coordinate data of defects, the repair system may not be able to locate pattern portions, or defects, to be repaired if they have shapes typical of recent fine patterns, which shapes are hard to identify. To overcome this problem, it is therefore an object of the present invention to provide an inspection system having a function to output information that allows easy identification of pattern portions to be repaired. Another object of the present invention is to provide an inspection method capable of improving yield and throughput of the entire manufacturing process by receiving information that allows easy identification of pattern portions to be repaired.

Other challenges and advantages of the present invention are apparent from the following description.

SUMMARY OF THE INVENTION

In accordance with the present invention, there is provided an inspection system comprising: an optical image capture unit configured to capture an optical image of an objected to be inspected by irradiating the object with light; a reference image generating unit configured to generate a reference image from design data of the object to be inspected; a comparing unit configured to compare the optical image with the reference image; and a data extracting unit configured to determine the coordinates of a portion determined to be a defect by the comparison, and further configured to extract data of a portion of predetermined dimensions containing the coordinates from the design data and output the extracted data.

In accordance with the present invention, there is also provided a method of inspecting an object to be inspected by comparing an optical image of the object with a reference image generated from design data of the object, the optical image being captured by irradiating the object with light, the method comprising: determining the coordinates of a portion determined to be a defect by the comparison; extracting data of a portion of predetermined dimensions containing the coordinates from the design data; and reinspecting only the portion of the predetermined dimensions.

BRIEF DESCRIPTION OF THE DRAWINGS

FIG. 7 is a schematic diagram showing a flow of data according to the second embodiment.

DETAILED DESCRIPTION OF THE EMBODIMENTS

First Embodiment

Figure 1:
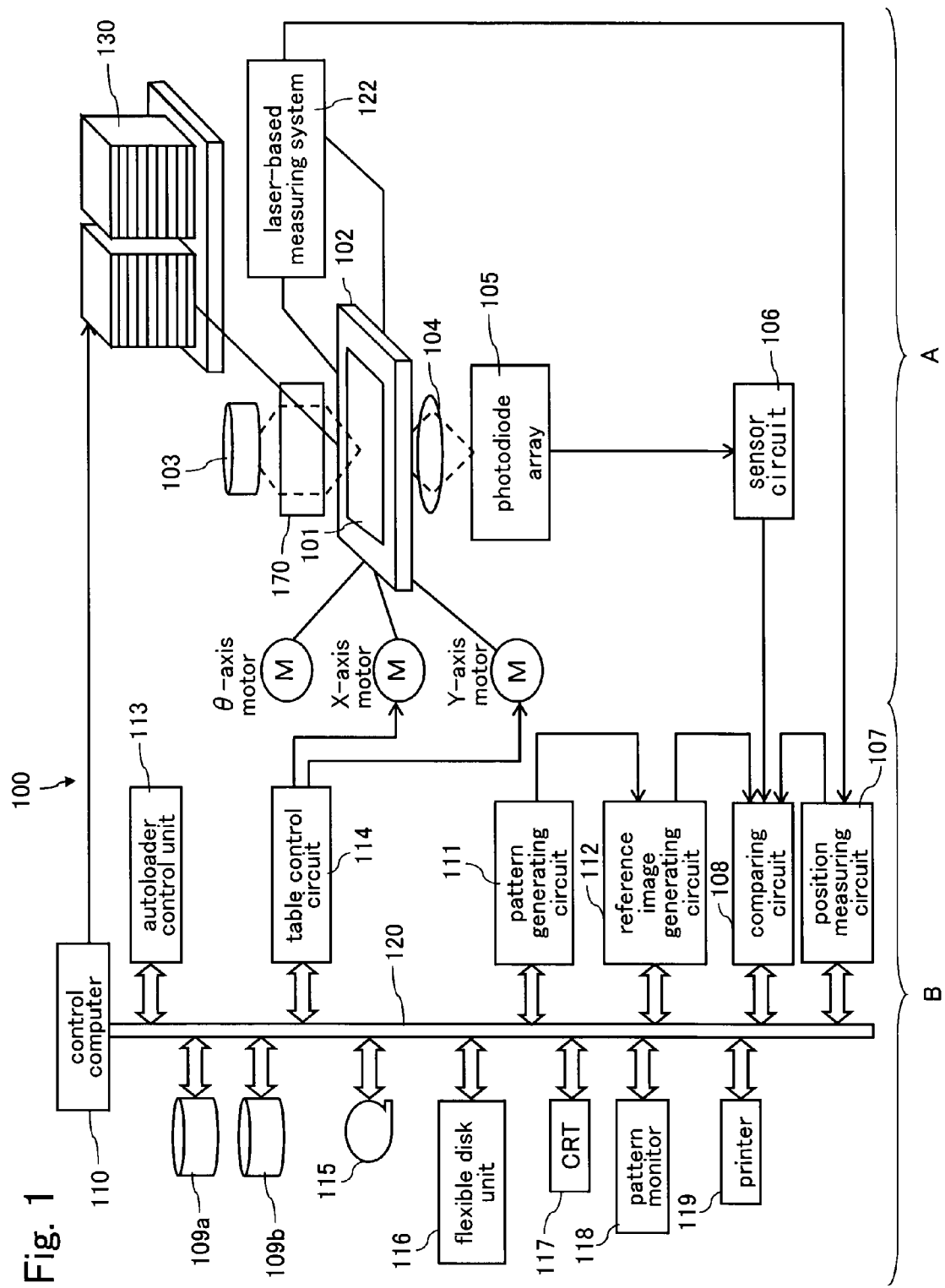
FIG. 1 is a diagram showing the configuration of an inspection system according to a first embodiment of the present invention.

FIG. 1 is a diagram showing the configuration of an inspection system according to an embodiment of the present invention. Although the inspection system of the present embodiment will be described in connection with the inspection of masks used in photolithography, it is to be understood that the system may be used to inspect wafers.

As shown in FIG. 1, the mask inspection system 100 includes an optical image capture unit A and a control unit B.

The optical image capture unit A includes a light source 103, an XYθ table 102 movable in the horizontal X and Y directions and rotatable in a horizontal plane (or in a θ direction), an illumination optical system 170 serving as a transmission illumination system, an enlarging optical system 104, a photodiode array 105, a sensor circuit 106, a laser-based measuring system 122, and an autoloader 130.

In the control unit B, a control computer 110 which controls the entire mask inspection system 100 is connected through a bus 120 (serving as a data transmission path) to a position measuring circuit 107, a comparing circuit 108, a reference image generating circuit 112, a pattern generating circuit 111, an autoloader control unit 113, a table control circuit 114, a first magnetic disk unit 109a and a second magnetic disk unit 109b serving as storage units, a magnetic tape unit 115, a flexible disk unit 116, a CRT 117, a pattern monitor 118, and a printer 119. The XYθ table 102 is driven by X-, Y-, and θ-axis motors controlled by the table control circuit 114. These motors may be, e.g., step motors.

Design pattern data which is used as reference data in die-to-database inspection is stored in the first magnetic disk unit 109a. This data is read out and sent to the pattern generating circuit 111 when necessary in the course of the inspection process. The pattern generating circuit 111 converts the design pattern data into image data (or bit pattern data). This image data is then sent to the reference image generating circuit 112 for generation of reference data.

It should be noted that the inspection system of the present embodiment may include, in addition to the components shown in FIG. 1 described above, other known components required to inspect masks. Further, although the present embodiment is described in connection with the die-to-database inspection method, it is to be understood that the embodiment may be applied to the die-to-die inspection method. In such a case, an optical image of one of two separate identical patterns on the mask is treated as a reference image.

Figure 2:
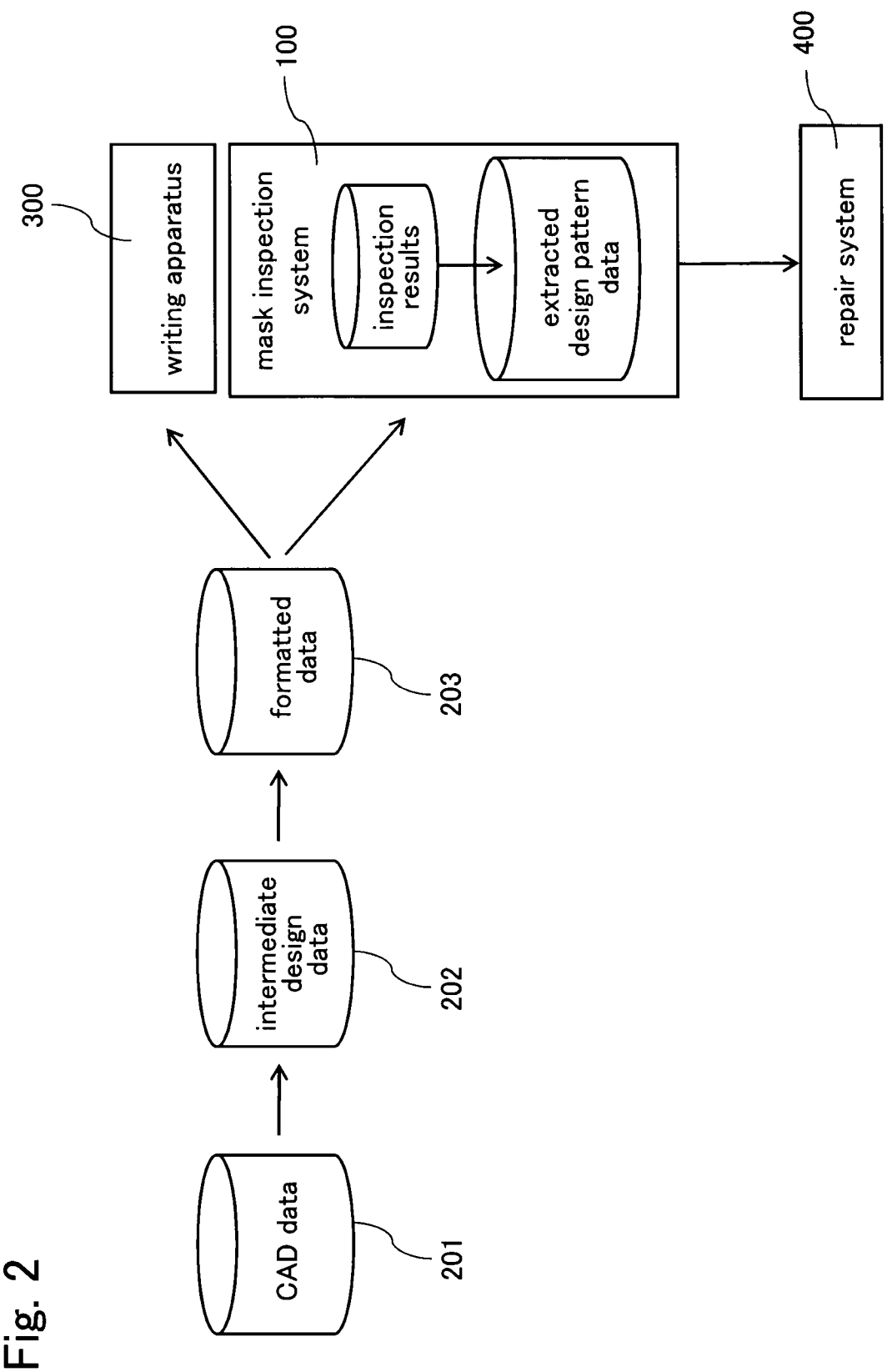
FIG. 2 is a schematic diagram showing a flow of data according to the first embodiment of the present invention.

FIG. 2 is a schematic diagram showing a flow of data according to the present embodiment.

As shown in FIG. 2, CAD data 201 prepared by the designer (or user) is converted to intermediate design data 202 in a hierarchical format such as OASIS. The intermediate design data 202 includes data of the pattern formed on the mask created for each layer. It should be noted that, generally, writing apparatuses are not adapted to be able to directly read OASIS data. That is, each manufacturer of writing apparatus uses different data format. Therefore, OASIS data is converted, for each layer, to data 203 in a format specific to the writing apparatus 300, and this formatted data 203 is input to the writing apparatus 300. Likewise, the mask inspection system 100 is also not adapted to be able to directly read OASIS data, and therefore receives the formatted data 203 compatible with the writing apparatus 300. It should be noted that the mask inspection system 100 may receive converted or formatted data in a format specific to the system.

Incidentally, the formatted data for the writing or inspection (or the original data such as GDS II data or OASIS data before it is converted into these formatted data) includes data of features for forming complicated pattern shapes provided to accurately control the line width and spacing of patterns written on the mask, as well as to accurately control the line width and spacing of dummy patterns formed to improve the resolution of the actual patterns. The volume of the resulting pattern data is huge, and therefore the writing apparatus and the inspection system are adapted to prevent a delay in the writing time and in the inspection time due to the increased volume of the pattern data. Specifically, the function to read pattern data and expand it is performed by a high speed, high capacity parallel processing computer in combination with a hard disk unit designed to accommodate the read rate required for the processing.

Figure 3:
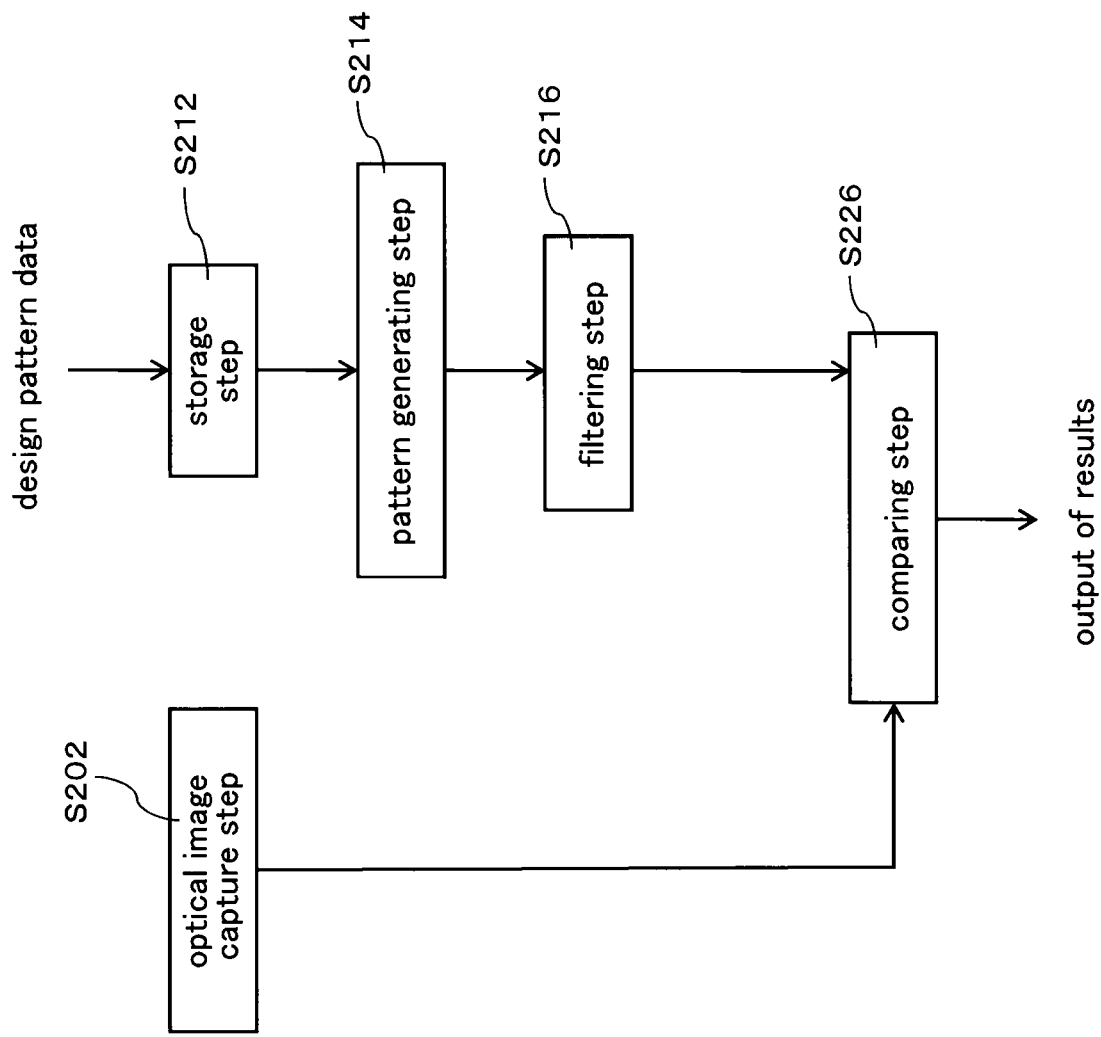
FIG. 3 is a flowchart showing an inspection process.

FIG. 3 is a flowchart showing an inspection process.

As shown in FIG. 3, this inspection process includes an optical image capture step (S202), a design pattern data storage step (S212), a pattern generating step (S214), a filtering step (S216), and a comparing step (S226), where the pattern generating step and the filtering step together form a design image data generating step.

At the optical image capture step S202, the optical image capture unit A shown in FIG. 1 captures an optical image (acquisition data) of a photomask 101. It will be noted that this optical image includes an image of a pattern on the mask, which pattern was written in accordance with the corresponding design pattern data. The detailed method of capturing this optical image is, e.g., as follows.

The photomask 101 serving as an inspection workpiece is mounted on the XYθ table 102 provided to be movable in two horizontal directions by X- and Y-axis motors and rotatable in a horizontal plane by a θ-axis motor. The pattern formed on the photomask 101 is then irradiated with light emitted from the light source 103 disposed above the XYθ table 102. More specifically, the beam of light emitted from the light source 103 passes through the illumination optical system 170 and shines on the photomask 101. The enlarging optical system 104, the photodiode array 105, and the sensor circuit 106 are disposed below the photomask 101. The light transmitted through the photomask 101 passes through the enlarging optical system 104 and reaches the photodiode array 105, thereby forming an optical image thereon. It should be noted that the enlarging optical system 104 may have its focus automatically adjusted by an autofocus mechanism (not shown). Further, though not shown, the mask inspection system 100 may be constructed such that light is also emitted from a source below the photomask 101, and the reflected light is passed through an enlarging optical system to a second photodiode array, thus capturing the transmitted light and the reflected light simultaneously. Further, the mask may be inspected using only transmitted light or reflected light depending on the film quality of the mask or the conditions of the pattern formed on the mask.

Figure 4:
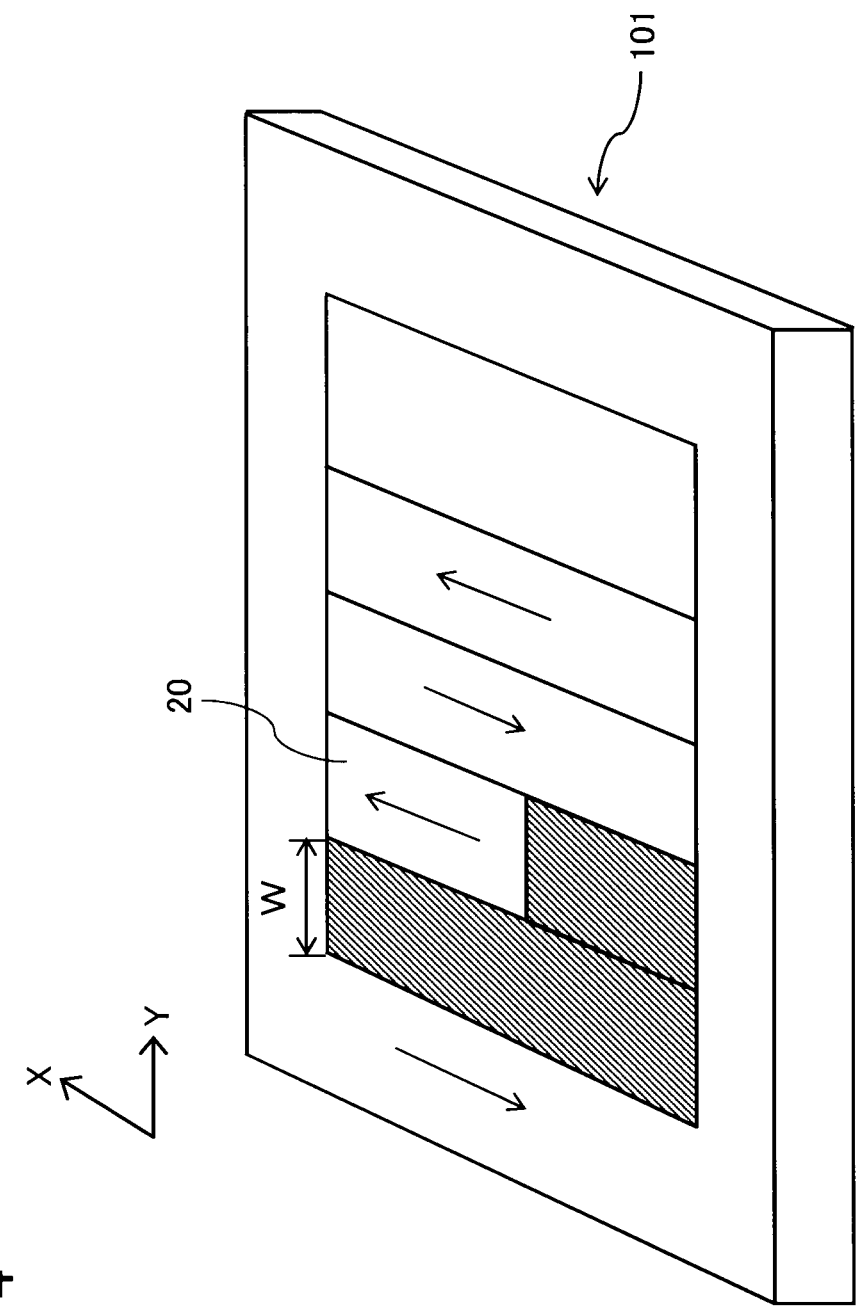
FIG. 4 is a diagram illustrating the way in which an optical image is captured.

FIG. 4 is a diagram illustrating the way in which an optical image is captured.

The inspection area is divided into a plurality of strip-shaped inspection stripes 20 by imaginary lines running in the X direction, where the width of each inspection stripe 20 in the Y direction is equal to the scan width W, as shown in FIG. 4. The movement of the XYθ table 102 is controlled so that each inspection stripe 20 is continuously scanned in the negative or positive X direction with the light to capture an image of the inspection stripe. At that time, the photodiode array 105 continuously generates an image (of each inspection stripe 20) having a width corresponding to the scan width W, as shown in FIG. 4. After capturing an image of the first inspection stripe 20 by scanning it, e.g., in the negative X direction, the second inspection stripe 20 is continuously scanned in the positive (i.e., opposite) X direction to capture an image of a width corresponding to the scan width W. Likewise, the third inspection stripe 20 is scanned in the negative x direction (opposite the direction in which the second inspection stripe 20 is scanned) to capture an image. This way of continuously capturing an image of one inspection stripe 20 after another reduces waste of processing time.

The pattern image formed on the photodiode array 105 is photoelectrically converted by the array 105 and A/D (analog to digital) converted by the sensor circuit 106. The photodiode array 105 is made up of sensors arranged in an array. These sensors may be, e.g., TDI (Time Delay Integration) sensors. Thus, the pattern on the photomask 101 is imaged by these TDI sensors while the XYθ table 102 is continuously moved in the positive or negative X direction. It will be noted that the light source 103, the enlarging optical system 104, the photodiode array 105, and the sensor circuit 106 together form a high power inspection optical system.

The XYθ table 102 can be moved in the X and Y directions and rotated in a θ direction (or in an XY plane) by a drive system such as a 3-axis (X-Y-θ) motor driven by the table control circuit 114 under the control of the control computer 110. These X-, Y-, and θ-axis motors may be, e.g., step motors. The position of the XYθ table 102 is measured by the laser-based measuring system 122, and the measurement data is sent to the position measuring circuit 107. Further, the photomask 101 is automatically loaded onto the XYθ table 102 from the autoloader 130 driven by the autoloader control circuit 113, and, upon completion of its inspection, the photomask 101 is automatically retrieved from the XYθ table 102.

The acquisition data (representing an optical image) output from the sensor circuit 106 is sent to the comparing circuit 108, together with data indicative of the position of the photomask 101 on the XYθ table 102, which data is output from the position measuring circuit 107. The acquisition data is, e.g., unsigned 8-bit data, representing the gray scale of each pixel.

At the storage step S212, the design pattern data that was used to form the pattern on the photomask 101 is stored in the first magnetic disk unit 109a serving as a storage unit.

The designed pattern includes pattern features each consisting of basic features such as rectangles and triangles. The first magnetic disk unit 109a stores feature data indicating the shape, size, and position of each pattern feature, specifically, e.g., information such as the coordinates (x, y) of the reference position of each feature, the length of its sides, and a shape code (or identifier) identifying the type of shape such as a rectangle or triangle.

Further, a group of pattern features defined in an area of approximately a few tens of micrometers square is referred to as a "cluster" or "cell." It is common practice that the design pattern data is defined in a hierarchical structure using clusters or cells. A cluster (or cell), which contains a pattern feature or features, may be used alone or repeated at certain intervals. In the former case the coordinate positions of the cluster (or cell) on the photomask are specified, whereas in the latter case the coordinate positions of each copy of the cluster (or cell) are indicated together with a repetition instruction. Each cluster (or cell) is disposed in a strip-shaped region, referred to as a "frame" or "stripe", having a width of a few hundreds of micrometers and a length of approximately 100 mm which corresponds to the length of the photomask in the X or Y direction.

At the pattern generating step S214, the pattern generating circuit 111 shown in FIG. 1 reads design pattern data of the photomask 101 from the first magnetic disk unit 109a through the control computer 110 and converts it into 2-bit or other multiple-bit image data (bit pattern data). This image data is sent to the reference image generating circuit 112.

Specifically, upon reading the design pattern data (serving as feature data), the pattern generating circuit 111 expands it to produce data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

At the filtering step S216, after receiving the design image data (i.e., image data of the pattern), the reference image generating circuit 112 performs appropriate filtering on the data.

Figure 5:
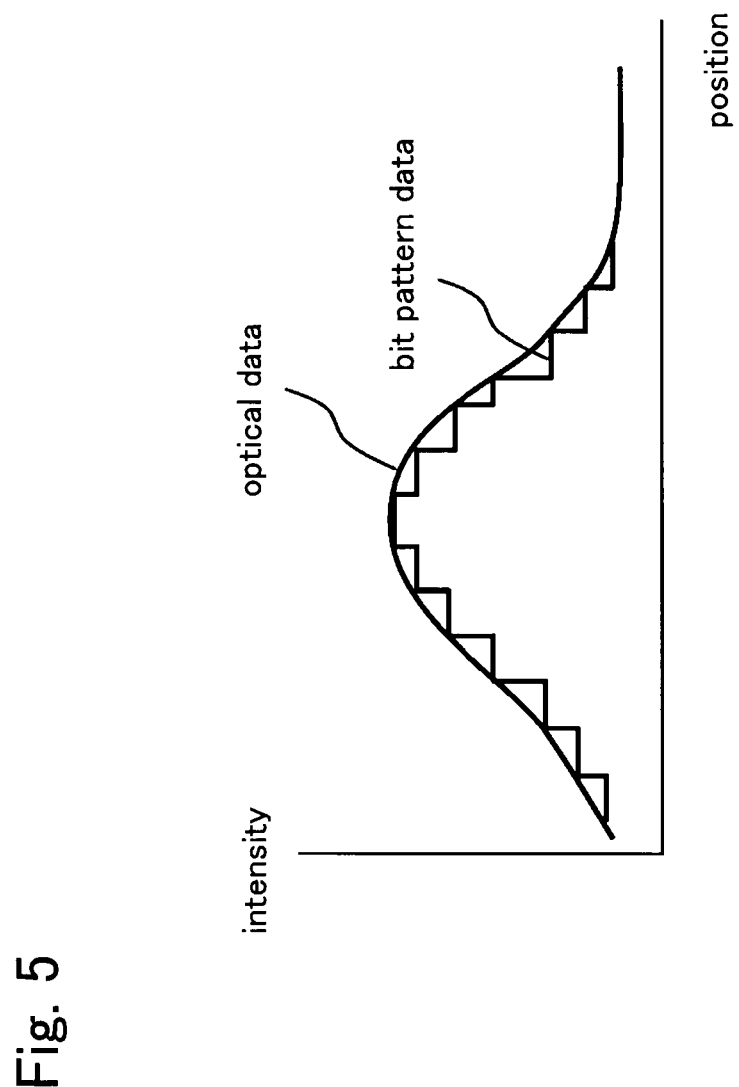
FIG. 5 is a diagram illustrating the filtering.

FIG. 5 is a diagram illustrating the filtering.

The optical image (or the acquisition data representing it) output from the sensor circuit 106 is somewhat "blurred" due to the resolution characteristics of the enlarging optical system 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or acquisition data. In this way, a reference image to be compared with the optical image is produced.

The acquisition data is sent to the comparing circuit 108, as described above. The design pattern data, on the other hand, is converted into design image data by the pattern generating circuit 111 and the reference image generating circuit 112, and then also sent to the comparing circuit 108.

The comparing circuit 108 compares each portion of the optical image received from the sensor circuit 106 with the corresponding portion of the reference image generated by the reference image generating circuit 112 in accordance with a suitable comparison determination algorithm, and if the difference (e.g., in dimension) between these portions exceeds a predetermined value, the comparing circuit 108 determines that the portion of the optical image is a defect. The optical image to be compared may be a transmitted image or a reflected image or a combination thereof, and the algorithm is selected to be suitable for the image to be compared. If it is determined from the comparison that a portion of the optical image is a defect, then the inspection system stores the coordinates of that portion and also stores image portions of predetermined dimensions extracted from the sensor capture image and the reference image on which the detection of the defect is based.

The operator reviews the detection results when the entire inspection region of the mask to be inspected has been inspected or when the inspection has been interrupted due to exceptional conditions or when a defect has been found.

The term "review" as used herein means an operation performed by the operator to determine whether a detected defect can be tolerated. Specifically, in order to check the coordinates of each detected defect of the mask, the operator displays an image of the defect by use of the observing optical system of the inspection system while moving the table on which the mask is mounted. At the same time the control computer screen of the inspection system displays, side-by-side, the defect identification criteria (or judgment conditions) and the stored observed mask image and reference image on which the detection of the defect is based. The operator reviews all the defects detected by the system, and if at least one of them requires repair, the mask is sent on to the repair process. At that time, the type of each defect (e.g., extrusion or intrusion, etc.) and its coordinates are also sent to the repair process, since different repair methods are used depending on whether it is a extrusion defect or intrusion defect. Further in accordance with the present embodiment, data required for visually recognizing areas of the pattern around the defect is extracted from the design pattern data and also sent to the repair system together with the sensor image captured by the mask inspection system 100, as shown in FIG. 2, in order to allow identification of the defect.

Such extraction from the design pattern data is accomplished as follows.

Figure 6A:
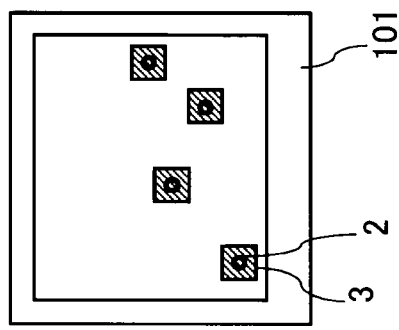
FIG. 6A is a diagram showing a design pattern.
Figure 6B:
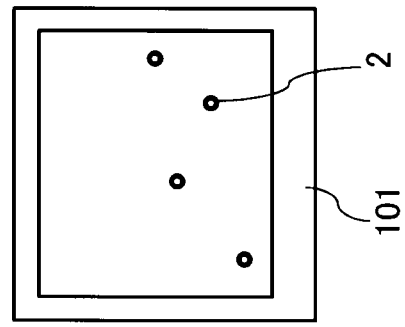
FIG. 6B is a diagram showing defects.
Figure 6C:
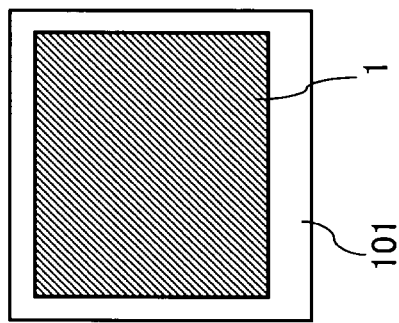
FIG. 6C is a diagram showing extracted data.

FIG. 6A is a diagram schematically showing a design pattern 1 written on the photomask 101. Further, FIG. 6B is a diagram schematically showing defects 2 detected on the photomask 101. The positions of these defects are defined, e.g., in an XY coordinate system with its origin located at the center of the mask. Further, the pattern data used in die-to-database inspection to generate a reference image, that is, the data shown in FIG. 6A, also describes geometries in the same XY coordinate system with its origin located at the center of the mask. (That is, the design pattern 1 shown in FIG. 6A is also expressed in the same XY coordinate system.) It should be noted that the geometry of the surface of the mask can be expressed in two XY coordinate systems as viewed from the glass surface and the film surface, respectively, of the mask; the positive direction of the X or Y axis of one XY coordinate system is opposite to that of the other (i.e., these XY coordinate systems are mirror images of each other). However, in this example, the coordinate positions of detected defects and the pattern in the database are expressed in the XY coordinate system as viewed from the glass surface of the mask. In accordance with the present embodiment, data required for visually recognizing areas 3 of the pattern around defects is extracted from the design pattern data based on the coordinates of the defects, as shown in FIG. 6C. The design pattern data is defined in a hierarchical structure made up of cluster data or cell data describing clusters or cells each including a group of pattern features. Clusters or cells are grouped into frames or stripes. The data of clusters, cells, frames, and stripes specifies their dimensions and shapes. For example, the data of a cluster specifies its shape (a rectangle), its dimensions, and its reference point (the lower left apex), etc.

The reference pattern image of a defect may extend over a plurality of clusters or cells, and even over a plurality of frames or stripes. Therefore, it is practical that the pattern area to be inspected around the defect (referred to herein as the "defect inspection pattern area") may be specified in the database by specifying a plurality of clusters or cells whose reference points are located less than a predetermined distance away from the position of the defect in the X and Y directions, instead of specifying each pattern feature in the defect inspection pattern area.

The inspection result information, which includes the coordinates of defects, and the design pattern data are stored in the first magnetic disk unit 109a. The data of the defect inspection pattern area for each defect is extracted from the design pattern data as follows. First, the control computer 110 determines the two X coordinate lines a predetermined distance away from the X coordinate line passing through the position of the defect and also determines the two Y coordinate lines a predetermined distance away from the Y coordinate line passing through the position of the defect. The control computer 110 then determines the clusters or cells whose reference points are located within the area defined and enclosed by these determined four coordinate lines, and extracts the data of these clusters or cells from the design pattern data read from the first magnetic disk unit 109a. The control computer 110 then generates an output file containing the extracted data. The output file is converted into the same format as the input design pattern data or into a GDS II format or OASIS format, which is highly versatile, before it is output to the second magnetic disk unit 109b.

The pattern data including only data of the area of the pattern around each detected defect (which data was formatted and output to the second magnetic disk unit 109b, as described above) is sent from the mask inspection system 100 to the repair system 400 via a network, a magnetic floppy disc, or any other detachable medium for use by the repair system 400, as shown in FIG. 2.

Second Embodiment

The inspection system of the first embodiment is adapted to send to the repair system, along with inspection results, an observed sensor image of each defect and databased design pattern data specifying the shape of an area of the pattern around the defect. On the other hand, a second embodiment of the present invention provides an inspection system adapted to send inspection results, etc. to a lithography simulator (or process simulator). It should be noted that the configuration of the inspection system of the present embodiment is the same as that shown in FIG. 1 and described in connection with the first embodiment.

In recent years, defects associated with micropatterns include not only shape defects typified by pattern edge roughness, but also pattern line width defects and spacing defects between adjacent patterns due to pattern displacement, which are becoming more and more significant. Therefore, there has been an extremely strong need to accurately control the dimensions of patterns, thus increasing the difficulty of manufacturing masks. As a result, there has been loss in the yield of masks that meet required specifications, thereby raising mask manufacturing cost. In order to address this problem, a defect evaluating method has been proposed which simulates the image which would be photolithographically printed from the mask to a wafer by the stepper and determines whether or not the pattern on the mask is defective by inspecting the simulated image.

For example, in die-to-die inspection, two or more separate corresponding (or supposedly identical) patterns on the mask are compared to each other to determine the difference (e.g., in dimension) between them. The inspection system then sends to the lithography simulator two images: a sensor image including an image of a pattern defect found in the inspection by the system and the corresponding reference sensor image. The lithography simulator then simulates the aerial image or the resist image of a wafer to which the pattern on the mask has been printed under predetermined stepper illumination conditions and lithography conditions. The simulator then compares the image simulated from the sensor image including the image of the pattern defect with the image simulated from the reference image to determine whether the defect can be tolerated.

In die-to-database inspection, on the other hand, there may be a method in which the inspection system sends to the lithography simulator a sensor image including an image of a pattern defect found in the inspection by the system and the corresponding reference data generated from the design pattern data. However, the following method of the present invention permits more accurate defect inspection. The inspection system sends to the lithography simulator extracted design pattern data specifying only an area of the pattern around the defect (i.e., a defect inspection pattern area), instead of sending the reference image generated by the inspection system to the simulator, and the lithography simulator then simulates, based on this extracted data, the aerial image or resist image of a wafer to which the pattern has been printed. The lithography simulator then performs die-to-database comparison using this simulated wafer image.

In the present embodiment, the extraction from the design pattern data is performed in the same manner as described in connection with the first embodiment. Specifically, first, design pattern data selected based on the coordinates of each defect found by the inspection system is read from the first magnetic disk unit 109a. Next, the control computer 110 determines the two X coordinate lines a predetermined distance away from the X coordinate line passing through the position of the defect and also determines the two Y coordinate lines a predetermined distance away from the Y coordinate line passing through the position of the defect. The control computer 110 then determines the clusters or cells whose reference points are located within the area defined and enclosed by these determined four coordinate lines, and extracts the data of these clusters or cells from the design pattern data read from the first magnetic disk unit 109a. The control computer 110 then generates an output file containing the extracted data. The output file is converted into the same format as the input design pattern data or into a GDS II format or OASIS format, which is highly versatile, before it is output to the second magnetic disk unit 109b.

FIG. 7 is a schematic diagram showing a flow of data according to the present embodiment.

As shown in FIG. 7, CAD data 201 prepared by the designer (or user) is converted to intermediate design data 202 in a hierarchical format such as OASIS. The intermediate design data 202 includes data of the pattern formed on the mask created for each layer. It should be noted that the mask inspection system 100 is not adapted to be able to directly read OASIS data, as described in connection with the first embodiment. Therefore, the mask inspection system 100 may receive the formatted data 203 compatible with the writing apparatus 300, or receive converted or formatted data in a format specific to the system.

The mask inspection system 100 sends to the lithography simulator 500 pattern data specifying only the defect inspection pattern area for each defect, as described above.

The mask inspection system 100 is connected to the lithography simulator 500 via a network such as Ethernet®, or directly via a dedicated data bus. This allows the mask inspection system 100 to send to the lithography simulator 500 the coordinates of each detected defect, the sensor image of the pattern, and the extracted design pattern data specifying the defect inspection pattern area for the defect. After receiving these data, the lithography simulator 500 generates an ideal wafer image corresponding to the defect inspection pattern area from the received design pattern data based on the received coordinates of the defect. Further, the lithography simulator 500 simulates, based on the mask sensor image received from the mask inspection system 100, the image of a wafer to which the mask image has been printed. The lithography simulator 500 then determines from the simulated image whether each defect found by the mask inspection system 100 can be tolerated (i.e., whether each possible defect found by the mask inspection system 100 is a real defect), and if the determination is no, the simulator sends information regarding this determination to the mask inspection system 100.

Of all the defects (or possible defects) found by the mask inspection system 100, those determined by the lithography simulator 500 to be intolerable may be primarily reviewed by the operator of the mask inspection system 100 to quickly determine whether the mask requires repair.

Third Embodiment

It is not necessary to accurately control the dimensions, etc. of all the patterns formed on a mask. For example, a dummy feature or pattern, which does not serve for wiring purposes, is sometimes formed in a place where the pattern density is extremely low. No problem is presented even if this dummy feature or pattern has some "pin-hole defect" or edge roughness.

On the other hand, it is necessary to accurately control the impedance of a pattern through which a clock signal passes (i.e., a clock line), and the position and the diameter of a contact hole passing through a plurality of layers.

In order to address this problem, a method has been proposed in which the level of importance, or weight, of each pattern is added to design pattern data as pattern importance information, and pattern data and pattern importance information are input to the inspection system. The present invention is also advantageous when applied to inspection systems adapted to use this method, that is, inspection systems capable of varying their inspection sensitivity in accordance with the level of importance of each pattern. The configuration of the inspection system of the present embodiment is the same as that shown FIG. 1 and described in connection with the first embodiment. Therefore, the present embodiment will be described with reference to FIG. 1.

For example, in the case where an inspection system is connected to a lithography simulator, as in the second embodiment, the lithography simulator simulates only or primarily the image of each defect area of each pattern with a high level of importance projected onto a wafer. This allows a reduction in the simulation and operation time, as well as allowing the operator to review primarily these important defect areas, which should be the first to be checked for tolerance.

The pattern importance information, together with the pattern data, is stored in the magnetic disk unit 109a shown in FIG. 1. At the pattern generating step, the mask inspection system 100 reads pattern data and pattern importance information from the magnetic disk unit 109a through the control computer 110 and creates image data representing the reference image and the corresponding pattern importance information. Specifically, the inspection system divides each pattern (represented by the pattern data) into an imaginary grid of squares (or grid elements) having predetermined quantization dimensions, and produces 2-bit or other multiple-bit design image data of the design pattern segment in each grid element. By using the produced design image data, the inspection system calculates the design pattern occupancy in each grid element (corresponding to a sensor pixel). This pattern occupancy in each pixel represents the pixel value.

The pattern importance information is converted into defect determination threshold values each to be applied to one element (or pixel) of the grid by which the pattern is divided. These defect determination threshold values are then sent to the comparing circuit 108. The comparing circuit 108 then determines whether the pattern segment represented by each pixel is a defect based on the defect determination threshold value for the pixel. The inspection system then stores the pattern importance information, in addition to conventional defect information, that is, the coordinates of each defect and the sensor image and the reference image of the mask on which the detection of the defect is based.

The databased pattern extracting function of the mask inspection system 100 can process the pattern data that was used to generate the reference image by use of which each pattern was inspected for defects by the inspection system, as well as being capable of extracting and outputting that portion of the inspection sensitivity-specifying pattern data which corresponds in coordinate position to and which is used and paired with the above pattern data. This data may be sent from the second magnetic disk unit 109b to the lithography simulator, as necessary, and used to help determine whether each detected defect can be tolerated based on the image of the defect projected onto a wafer.

The inspection system sends the data of the detected defects to the lithography simulator sequentially in the order of decreasing importance so that the lithography simulator can determine whether each defect can tolerated based on the image of the defect projected onto a wafer. The determination results are sequentially sent back to the inspection system. This allows the operator to review primarily defects with a high level of importance so as to quickly determine whether the mask under inspection requires repair.

As described above, in order to allow external devices, such as repair systems and the lithography simulators, to identify a pattern defect detected in inspection, the inspection systems of the present invention extract from the design pattern data the data required for visually recognizing areas of the pattern around the defect and send the extracted data to these external devices in addition to the sensor image captured by the inspection systems, thus ensuring efficient data exchange with the external devices. Further, the inspection systems output information that allows easy identification of pattern portions requiring repair, resulting in improved yield and throughput of the entire manufacturing process.

The features and advantages of the present invention may be summarized as follows.

The inspection system of the present invention can output information that allows easy identification of pattern portions to be repaired.

The inspection method of the present invention can improve yield and throughput of an entire mask manufacturing process by reinspecting the pattern after receiving information that allows easy identification of pattern portions to be repaired.

The present invention is not limited to the aforementioned embodiment. Various changes and modifications can be made without departing from the gist of the present invention.

For example, in the review process each detected defect of the mask is examined to determine whether it requires repair, and upon the completion of this process, the mask is sent to the repair process. After the completion of the repair, the mask is reinspected by the inspection system to determine whether the correct repair has been made to the mask. It will be noted that at that time the inspection system may inspect only the repaired portions of the mask, instead of reinspecting the entire surface of the mask, thereby greatly reducing the inspection time. This may be accomplished by use of the design pattern extracted by the design pattern extracting function of the present invention. That is, the inspection system may be adapted to be able to use the results of the first inspection when reinspecting the mask after it is repaired. This allows the inspection system to obtain the coordinates of the defect areas to be reinspected and the extracted design pattern data corresponding to these areas (or coordinates) and inspect only a pattern area of predetermined dimensions around each defect in a short time.

In the manufacture of masks in which a plurality of inspection systems are used, the inspection system that initially inspects a mask cannot necessarily be used to reinspect the mask after repair of the mask. Therefore, when the inspection system that initially inspects the mask is different from the inspection system that reinspects it, these inspection systems may be designed to exchange and use the inspection results and the design pattern data file containing only the extracted data of the defect inspection pattern areas. This ensures efficient data transmission between these inspection systems, since this design pattern data file is smaller in size than that containing the data of the entire pattern.

It should be noted that if the inspection system that initially inspected the mask does not have the above function of the present invention (and the inspection results including the coordinates of the defects and the design pattern data are still available), the design pattern extracting function of the present invention may be used to extract the design pattern data corresponding to the defect inspection pattern areas after repairing the mask and before reinspecting it. In this case, the inspection system that initially inspected the mask reads and sends the design pattern data and the coordinates of the defects through a network to the data storage unit of the inspection system which is to reinspect the mask after it is repaired. The design pattern extracting function may run on the inspection system which reinspects the mask after it is repaired, or run on the master control computer operating as a server to supply design pattern data to a plurality of inspection systems.

Further, in the case where pattern importance information is added to the design pattern data, the operator may specify that the lithography simulator should determine whether a particular portion of a pattern includes a defect. That is, if, due to the features of the pattern, there is not much margin for pattern edge roughness or variation in the printing and lithography process, the lithography simulator might determine the pattern (or a particular portion thereof) to be defective even if the inspection system determined it to be not defective. Therefore, it is preferable that the inspection system stores the specified coordinates and the corresponding defect information and outputs them to the lithography simulator, regardless of the defect determination by the inspection system.

The databased pattern extracting function of the present invention may be activated to read and process the defect information and databased pattern data about a mask after the completion of the inspection of the mask. Alternatively, each time the inspection system detects a defect or each time the inspection of the mask has progressed by a predetermined amount, the function may be activated to read the defect information obtained during that period and also read databased pattern data for operation. It should be noted that the above predetermined amount of progress in the inspection may be such that the databased pattern extracting function is activated each time a predetermined number of stripes (or strip-shaped regions) in the inspection region have been scanned and inspected (where the inspection region is divided into stripes), or each time a predetermined amount of area of the inspection region has been inspected or the number of detected defects has exceeded a predetermined value.

The databased pattern extracting function may extract the data of an area centered around each defect and having dimensions as determined by the tolerance. It should be noted that if the pattern data has a hierarchical format, the function preferably follows the hierarchical structure when extracting the data of an area centered around each defect and having dimensions as determined by the tolerance.

Furthermore, the above description of the present embodiment has not specified apparatus constructions, control methods, etc. which are not essential to the description of the invention, since any suitable apparatus constructions, control methods, etc. can be employed to implement the invention. Further, the scope of this invention encompasses all pattern inspection systems and pattern inspection methods employing the elements of the invention and variations thereof which can be designed by those skilled in the art.

Obviously many modifications and variations of the present invention are possible in the light of the above teachings. It is therefore to be understood that within the scope of the appended claims the invention may be practiced otherwise than as specifically described.

The entire disclosure of a Japanese Patent Application No. 2009-189606, filed on Aug. 18, 2009 including specification, claims, drawings and summary, on which the Convention priority of the present application is based, are incorporated herein by reference in its entirety.

What is claimed is:

1. An inspection system comprising:
an optical image capture unit configured to photoelectrically capture an optical image of an object to be inspected by irradiating said object with light;
a reference image generating unit configured to generate a reference image from design data that was used to form a pattern on said object to be inspected;
a reference image filtering unit configured to change a resolution characteristic of the reference image to generate a filtered reference image;
a comparing unit configured to compare said optical image with said filtered reference image; and
a data extracting unit configured to determine the coordinates of a portion of the pattern on said object determined to be defective by said comparison, and further configured to extract an extracted design data portion including only data of the pattern around each detected defect of predetermined dimensions corresponding to said coordinates from said design data, as well as configured to extract a portion of inspection sensitivity-specifying pattern data paired with said extracted design data portion, then output said extracted design data portion and said extracted sensitivity-specifying pattern data portion, and determine whether to perform a lithography simulation of a detected defect based on the data of the pattern around the detected defect and the inspection sensitivity-specifying pattern data portion paired with the extracted design data portion.

2. The inspection system according to claim 1, wherein said data extracting unit is further configured to convert design data in a predetermined format into a different format.

3. The inspection system according to claim 1, further configured to reinspect only said extracted design data portion extracted by said data extracting unit.

4. The inspection system according to claim 1, wherein said data extracting unit is activated when the inspection of said object to be inspected has been completed, when said defect has been detected, or each time said inspection has progressed by a predetermined amount.

5. The inspection system according to claim 2, further configured to reinspect only said extracted design data portion extracted by said data extracting unit.

6. The inspection system according to claim 2, wherein said data extracting unit is activated when the inspection of said object to be inspected has been completed, when said defect has been detected, or each time said inspection has progressed by a predetermined amount.

7. The inspection system according to claim 3, wherein said data extracting unit is activated when the inspection of said object to be inspected has been completed, when said defect has been detected, or each time said inspection has progressed by a predetermined amount.

8. The inspection system according to claim 1, wherein the reference image filtering unit is further configured to change the resolution characteristic of the reference image based on resolution characteristics of an enlarging optical system in the optical image capture unit and an aperture effect of a photodiode array in the optical image capture unit.

9. The inspection system according to claim 1, wherein the reference image filtering unit is further configured to generate the filtered reference image by applying a spatial low-pass filter to the reference image.

10. The inspection system according to claim 1, wherein the data extracting unit is further configured to output the extracted design data portion and said extracted sensitivity-specifying pattern data portion sequentially in the order of decreasing importance.

11. A method of inspecting an object, said method comprising:
    capturing, using a photoelectric optical image capture unit, an optical image of said object by irradiating said object with light;
    generating a reference image from design data that was used to form a pattern on said object;
    generating a filtered reference image from the reference image by changing a resolution characteristic of the reference image;
    comparing the optical image of said object with the filtered reference image;
    determining the coordinates of a portion of the pattern on said object determined to be a defect by said comparing;
    extracting an extracted design data portion including only data of the pattern around each detected defect of predetermined dimensions corresponding to said coordinates from said design data, as well as extracting an inspection sensitivity-specifying pattern data portion paired with said extracted design data portion;
    determining whether to perform a lithography simulation of a detected defect based on the data of the pattern around the detected defect and the inspection sensitivity-specifying pattern data portion paired with the extracted design data portion; and
    reinspecting only said extracted design data portion of said predetermined dimensions.

12. The method according to claim 11, wherein said extracting is performed when the inspection of said object to be inspected has been completed, when said defect has been detected, or each time said inspection has progressed by a predetermined amount.

13. The method according to claim 11, further comprising:
    when a first inspection system that captures said optical image and compares said optical image with said reference image is different from a second inspection system that reinspects said portion of said predetermined dimensions, transferring data between said inspection systems.

14. The method according to claim 11, wherein the changing the resolution characteristic of the reference image is performed based on resolution characteristics of an enlarging optical system used in the capturing and an aperture effect of a photodiode array used in the capturing.

15. The method according to claim 11, wherein the generating the filtered reference image includes applying a spatial low-pass filter to the reference image.

16. The method according to claim 11, further comprising:
    outputting the extracted design data portion and said extracted sensitivity-specifying pattern data portion sequentially in the order of decreasing importance.

* * * * *